(12) United States Patent
Okuda et al.

(10) Patent No.: US 8,022,362 B2
(45) Date of Patent: Sep. 20, 2011

(54) IONIZATION DEVICE

(75) Inventors: Daiji Okuda, Kyoto (JP); Shigeru Kimoto, Kyoto (JP); Hiroshi Okuda, Kyoto (JP); Motoaki Adachi, Osaka (JP)

(73) Assignees: Shimadzu Corporation, Kyoto (JP); Osaka Prefecture University Public Corporation, Osaka (JP)

( * ) Notice: Subject to any disclaimer, the term of this patent is extended or adjusted under 35 U.S.C. 154(b) by 269 days.

(21) Appl. No.: 12/520,536

(22) PCT Filed: Dec. 13, 2007

(86) PCT No.: PCT/JP2007/074000
§ 371 (c)(1),
(2), (4) Date: Jun. 20, 2009

(87) PCT Pub. No.: WO2008/075607
PCT Pub. Date: Jun. 26, 2008

(65) Prior Publication Data
US 2009/0314953 A1    Dec. 24, 2009

(30) Foreign Application Priority Data

Dec. 20, 2006 (JP) ................................ 2006-342110

(51) Int. Cl.
*H01J 49/14* (2006.01)
*H01J 37/317* (2006.01)
*H01J 37/04* (2006.01)

(52) U.S. Cl. ............... 250/288; 250/281; 250/492.1; 250/492.21; 313/362.1; 315/111.01; 427/569

(58) Field of Classification Search .............. 250/288, 250/281, 492.1, 492.21; 313/362.1; 315/111.01; 427/569
See application file for complete search history.

(56) References Cited

U.S. PATENT DOCUMENTS

| 4,339,782 | A |   | 7/1982 | Yu et al. |
| 5,554,255 | A | * | 9/1996 | Karner et al. ............... 427/569 |

(Continued)

FOREIGN PATENT DOCUMENTS

JP        11-176375 A        7/1999

(Continued)

OTHER PUBLICATIONS

International Search Report for the Application No. PCT/JP2007/074000 mailed Feb. 19, 2008.

(Continued)

*Primary Examiner* — Nikita Wells
(74) *Attorney, Agent, or Firm* — Cheng Law Group, PLLC

(57) ABSTRACT

An ionization device includes an ionization chamber (1) and a charging chamber (20) separately prepared therefrom. The ionization chamber (1) has a discharge electrode (6) and an opposing electrode (10) in an interior (4) of a case having an ionizing gas introducing inlet (14). The opposing electrode (10) has an orifice (8) communicating with outside and formed at a position opposing the tip end of the discharge electrode (6). The charging chamber (20) is arranged adjacent to the orifice (8) side of the ionization chamber (1). An introduction inlet (28) of a charge object introduction portion of the charging chamber (20) is arranged at the position near the exit of the orifice (8). The size of the orifice (8) is set so that the charge object is sucked therein by a negative pressure generated when a gas containing ions is sprayed from the exit of the orifice (8) into the charging chamber (20) and the ionization chamber (1) has a higher pressure than the charging chamber (20).

5 Claims, 2 Drawing Sheets

U.S. PATENT DOCUMENTS 7,022,981 B2 * 4/2006 Kato ............................. 250/288
7,022,999 B2 * 4/2006 Horsky et al. ................. 250/427

FOREIGN PATENT DOCUMENTS

| JP | 2003-326192 A | 11/2003 |
|---|---|---|
| JP | 2005-24409 A | 1/2005 |
| JP | 3787773 B2 | 4/2006 |
| JP | 2006-322899 A | 11/2006 |

OTHER PUBLICATIONS

Adachi, M. et al., "Unipolar and Bipolar Diffusion Charging of Ultrafine Aerosol Particles", J. Aerosol Sci., 1985, vol. 16, No. 2, pp. 109-123.

* cited by examiner

IONIZATION DEVICE

TECHNICAL FIELD

The present invention relates to an ionization device that is used for ionizing a measuring object and a film-forming substance in an analyzer and a film-forming device, such as a DMA (Differential Mobility Analyzer) for classifying particles in a gaseous phase and for measuring the grain-size distribution thereof, an electrostatic vapor deposition system (technique for arranging nano-sized functional material particles only on designed portions on a substrate by using an electric function), or a GC/MS (Gas Chromatography/Mass Analyzing) device.

BACKGROUND ART

An ionization device has been proposed (see Patent Document 1) in which a needle-shaped discharge electrode is installed in an inner space of a case, with an electrode having an orifice being placed at a position opposing the tip end of the discharge electrode and an enlarged pipe that expands in a reverse tapered state from the orifice toward the outside space, and a gas containing molecules of a predetermined substance is supplied to the inside of the case. In this ionization device, a gas containing molecules of a predetermined substance is supplied into the case, and a predetermined voltage is applied between the two electrodes to generate a discharge so that molecules of the gas inside the case are ionized and discharged from the orifice toward the outer space. Here, water is used as molecules to be ionized, and cluster ions derived from water macromolecules are generated in the outer space. In this ionization device, it is considered that an abrupt pressure reduction occurs by a high-speed jet air discharged from the enlarged pipe to cause a heat-insulated expansion to form a supersaturated atmosphere, with the result that water molecules in the atmosphere aggregate to form water molecular ions to be grown into large water cluster ions.

In the proposed ionization device, by carrying out a discharge in the inner space of the case, the ionization and the charging process to the molecules of the predetermined substance are executed in the same space.

Another ionization device has been proposed (see Patent Document 2) in which, in order to measure fine particles in an exhaust gas, a charging device is installed in the middle of an exhaust-gas introducing pipe, and a corona discharge is exerted inside the charging device so that fine particles in the exhaust gas passing therethrough are charged. In this ionization device also, the object fine particles to be ionized are directly charged in the charging device by the corona discharge.

Patent Document 1: Japanese Patent No. 3787773
Patent Document 2: JP-A No. 2005-24409
Non-Patent Document 1: J. Aerosol Sci., Vol. 16, No. 2, pp. 109-123, 1985

DISCLOSURE OF THE INVENTION

Problem to be Solved by the Invention

In the conventional ionization devices as described above, for example, in the corona discharge system, a charge object is introduced into a space in which a discharge process is carried out; however, in the case where a fragile charge object exists therein, the object might be damaged by the discharge process. Moreover, in the case where a highly reactive gas, such as sulfur dioxide, exists therein, particles other than the target particles might be generated. In such systems using soft X-rays and a micro-discharge process as well, the same problems are raised because the ion generation and charging process are carried out in the same space.

Moreover, in the case of the charging chamber with a large capacity, when a mono-polar charging process that allows only one kind of positive or negative ions to be generated is used, an ion concentration is reduced to a great degree because the generated ions are diffused and captured by a generated electric field, and when a bi-polar charging process that allows positive and negative ions to be generated is used, the ion concentration is also reduced to a great degree because the ions of the repulsive polarities are re-coupled, with the result that the charging efficiency is lowered.

The present invention aims to provide an ionization device that can solve the above problems of damages to the charge object and generation of particles other than the target particles, and can improve the charging efficiency.

Means for Solving the Problem

In order to solve these prior-art problems, by separating a mechanism for generating ions and a mechanism for carrying out a charging process from each other, the present invention makes it possible to solve the problems of damages to the charge object and generation of particles other than the target particles, and by narrowing the distance in which the generated ions are made in contact with the charge object, the present invention also makes it possible to suppress reduction in the ion concentration due to diffusion and re-coupling.

In other words, the ionization device of the present invention is provided with an ionization chamber and a charging chamber separately prepared therefrom. An ionization chamber is provided with a discharge electrode and an opposing electrode installed inside a case having an ionization gas introducing inlet, with an orifice, which communicates with the outside of the ionization chamber, being formed through the opposing electrode at a position opposing a tip end of the discharge electrode. A charging chamber is disposed adjacent to the ionization chamber on the orifice side thereof. The charging chamber has a charge object introduction portion and the charge object introduced from the charge object introduction portion is charged by ions discharged from the orifice to be formed into ions. The introducing inlet of the charge object introduction portion of the charging chamber is disposed close to the outlet of the orifice. The size of the orifice and the pressure between the ionization chamber and the charging chamber are so set that the charge object is sucked into the charging chamber by a negative pressure generated when a gas containing ions is sprayed from the exit of the orifice into the charging chamber with the pressure of the ionization chamber higher than that of the charging chamber.

A gas containing ions generated in the ionization chamber is sprayed into the charging chamber from the outlet of the orifice so that negative pressure is generated in the charge object introduction portion, and the charge object is sucked into the charging chamber together with the gas containing ions, and charged by the ions in the gas sprayed from the outlet of the orifice.

The charge object introduction portion is preferably arranged so as to introduce the charge object in a direction orthogonal to the spraying direction of ions by the orifice. With this arrangement, the charge object is smoothly sucked by the negative pressure generated by the gas containing ions that has been sprayed into the charging chamber from the outlet of the orifice.

In order to allow the ionization chamber to have a higher pressure than that of the charging chamber, the ionization chamber is pressurized, or the charging chamber is provided with a suction pump installed on the downstream side thereof, or both of the structures are prepared.

Effects of the Invention

In the present invention, the ionization chamber for generating ions and the charging chamber for charging the charge object by ions generated in the ionization chamber are formed differently from each other so that, in comparison with a system in which the ionization and the charging process are carried out in the same space, it becomes possible to suppress the damages to the charge object and generation of particles other than the target particles.

Moreover, since the introducing inlet of the charge object introduction portion of the charging chamber is disposed close to the outlet of the orifice of the ionization chamber, in the charging chamber, the charge object, sucked by negative pressure near the orifice outlet of the ionization chamber, is allowed to intersect with a flow of ions right below the orifice outlet of the ionization chamber so that it becomes possible to charge the charge object prior to reduction in ion concentration due to diffusion and re-coupling, and consequently to improve the charging efficiency.

Moreover, since the introducing inlet of the charge object introduction portion of the charging chamber is disposed close to the orifice outlet of the ionization chamber, it becomes possible to miniaturize the ionization device.

DESCRIPTION OF THE REFERENCE NUMERALS

Figure 1:
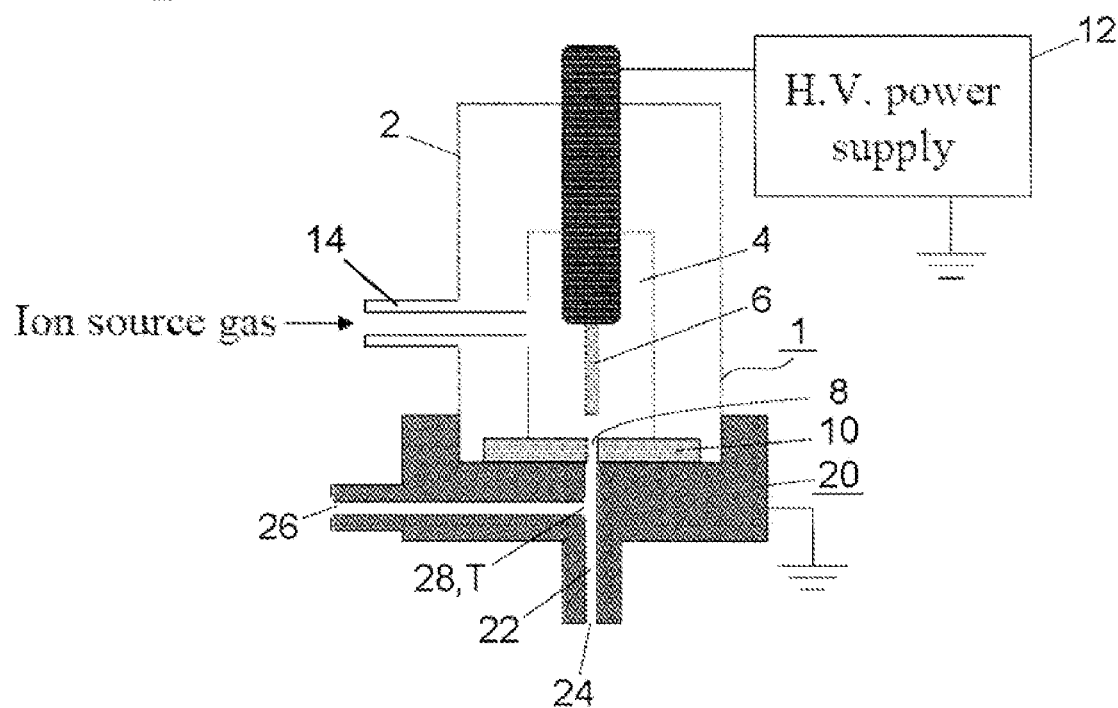
FIG. 1 is a cross-sectional view that schematically shows one embodiment of the present invention.

1 Ionization chamber
4 Inner space
6 Discharge electrode
8 Orifice
10 Opposing electrode
12 High voltage power supply
14 Ion source gas introduction portion
20 Charging chamber
22 Charging chamber inner space
26 Charging object introduction portion
28 Charging object introduction inlet

DETAILED DESCRIPTION OF THE INVENTION

FIG. 1 schematically shows an ionizing device in accordance with one embodiment. A needle-shaped discharge electrode 6 is installed in an inner space 4 of a case 2 of an ionization chamber 1, and an orifice 8 is formed through a wall at a position opposing the tip end of the discharge electrode 6. The wall 10 in which the orifice 8 is formed serves as an opposing electrode made from a conductive substance. The discharge electrode 6 is connected to an AC or DC high voltage power supply 12, and the opposing electrode 10 is grounded. A gas introduction portion 14, used for introducing, for example, air to the inner space 4 of the case 2 as an ion source gas, is formed. The case 2, the discharge electrode 6, the orifice 8, the opposing electrode 10 and the gas introduction portion 14 constitute the ionization chamber 1.

The distance between the discharge electrode 6 and the opposing electrode 10 is properly set to 1 to 3 mm. In the case where the distance between the discharge electrode 6 and the opposing electrode 10 is smaller than 1 mm, the ionized region becomes narrower; in contrast, in the case where the distance becomes greater than 3 mm, the discharge amount is lowered, with the result that either of the cases causes reduction in ionization efficiency.

Since the peripheral portion of the orifice 8 of the opposing electrode 10 is susceptible to damages due to corona discharge, the material of the opposing electrode 10 is preferably selected from those materials having an oxidation resistant property, and, for example, stainless and titanium are preferably used.

A charging chamber 20 is placed adjacent to the ionization chamber 1. The charging chamber 20 has a charging chamber inner space 22 that communicates with the outlet of the orifice 8 of the ionization chamber 1, and the inner space 22 is provided with an outlet 24 on the side opposing the orifice 8. The outlet 24 is connected to a device such as an analyzer or a film-forming device that analyzes or utilizes charged particles, An introduction portion 26 that introduces a charge object to the charging chamber 20 is designed so as to have an introducing inlet 28 at a position close to the outlet of the orifice 8.

A suction pump is placed on the downstream side of the charging chamber 20, or a pump is placed in a passage used for supplying an ion source gas to the ionization chamber 1, or both of these are installed, so as to make the pressure of the inner space 4 of the ionization chamber 1 higher than that of the inner space 22 of the charging chamber 20. The orifice 8 is designed so that the gas is sprayed from the ionization chamber 1 toward the charging chamber 20 by the pressure difference between the ionization chamber 1 and the charging chamber 20 through the orifice 8, and the orifice 8 is formed into such a small size as to cause negative pressure at the outlet of the orifice 8 by the gas spray.

The thickness of a flow caused when the gas containing the charge object is sucked and introduced through the charge object introducing inlet 28 by the negative pressure, that is, the thickness T of the charge object introducing inlet 28 relative to the gas spraying direction from the orifice 8, is set to a sufficiently thin level. The speed of the gas spray from the orifice 8 and the dimension of the charge object introducing inlet 28 are preferably set so that, when the charge object is sucked into the gas flow containing ions sprayed from the orifice 8, with such a thin thickness, the charging rate is allowed to attain equilibrium in a short period of time, such as, for example, in 10 milliseconds or less. The thickness T of the charge object introducing inlet 28 is set to, for example, 5 mm or less, preferably, in a range from 0.5 to 1 mm.

In the charge object introducing inlet 28, the orientation of the outlet is arranged so that the gas containing the charge object to be supplied from the introduction portion 26 is supplied in a direction orthogonal to the flow of the sprayed gas from the orifice 8 of the ionization chamber.

The shape of this charge object introduction portion 26 can be designed to an optimal shape in accordance with conditions, such as the dimension of the orifice 8, the dimension of the introducing inlet 28 and the gas flow rate of the gas sprayed from the orifice 8.

In this ionization device, for example, air serving as an ion source gas is introduced into the inner space 4 of the ionization chamber from the introducing inlet 14, and a high voltage is applied between the electrodes 6 and 10 by the power supply device 12 so that a corona discharge is generated. Thus, oxygen or nitrogen is ionized in the ionization chamber 1, and the resulting high-speed jet or sound-velocity jet is sprayed into the charging chamber 20 from the orifice 8 together with air that has not been ionized. A gas containing, for example, NaCl vapor, as the charge object is supplied into the charge object introduction portion 26. The gas containing the charge object is sucked into the charging chamber 20 by the negative pressure caused by the gas spray from the orifice 8 into the charging chamber 20, and charged by ions sprayed from the ionization chamber 1, and then supplied to the analyzing device and the like through the outlet 24.

Figure 2:
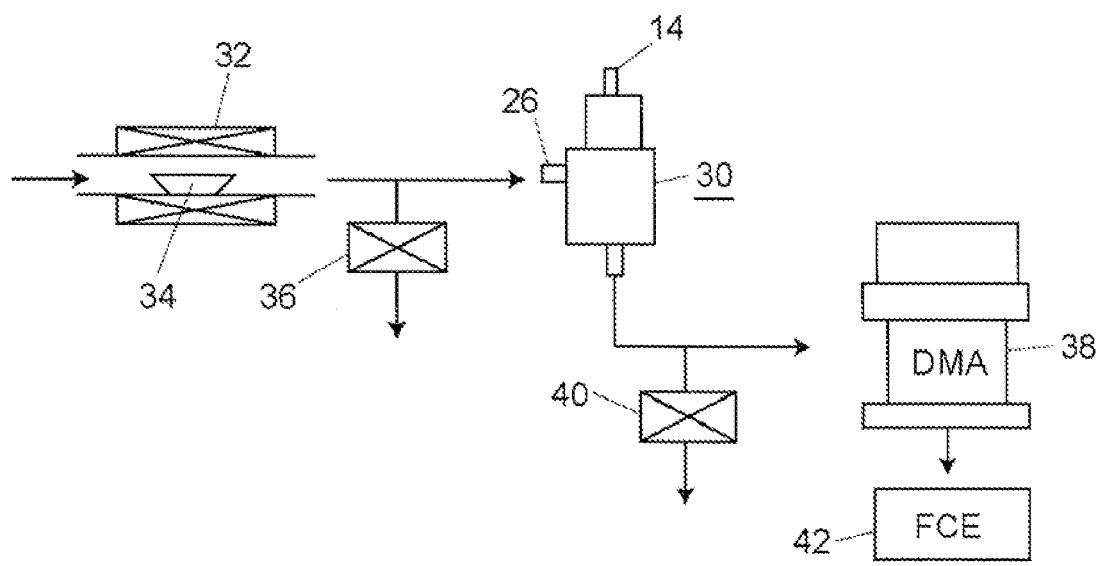
FIG. 2 is a schematic structural diagram that schematically shows a system used for measuring processes in which a charging object is ionized by using an ionization device of the present invention, and classified to be measured.

FIG. 2 schematically shows a system used for measuring processes in which a charging object is ionized by using this ionization device, and classified to be measured. The ionization device of the present invention is indicated by reference numeral 30. In order to supply the charge object into the ionization device 30, a boat 34, made of quartz, in which sodium chloride (NaCl) serving as a charge object is put in an electric furnace 32, is disposed, and nitrogen is sent to the electric furnace as a carrier gas so that a gas from the electric furnace is supplied to the ionization device 30. In the middle of the passage from the electric furnace 32 to the ionization device 30, an exhaust pump 36 for use in splitting is installed. In the passage through which the gas containing the charge object ions, ionized in the ionization device 30, is supplied to the analyzer 38, an exhaust pump 40 for use in splitting is also installed. As the analyzer 30, for example, a DMA is used, and fine particle ions, classified by the DMA 38, are detected by a Faraday cup detector 42 serving as the detector.

In this analyzing system, for example, nitrogen is supplied to the electric furnace 32 as a carrier gas, and in the electric furnace 32, NaCl is heated to 600° C. and sublimated. While one portion of the nitrogen gas containing sublimated NaCl vapor is being exhausted from the exhaust pump 36, the resulting gas is adjusted to a flow rate of 1 L/min, and supplied through the charge object introduction portion 26 of the ionization device 30. In the ionization device 30, air serving as an ion source gas is supplied into the ionization chamber at a flow rate of 2 L/min from the supply inlet 14, while being pressurized to 0.2 MP, and ionized. The gas containing NaCl ions, sent from the ionization device 30, has a flow rate of 3 L/min, and a portion corresponding to 2 L/min of this is removed by the exhaust pump 40, and the rest of the gas corresponding to 1 L/min is supplied to the DMA 38 so as to be classified and detected.

Figure 3:
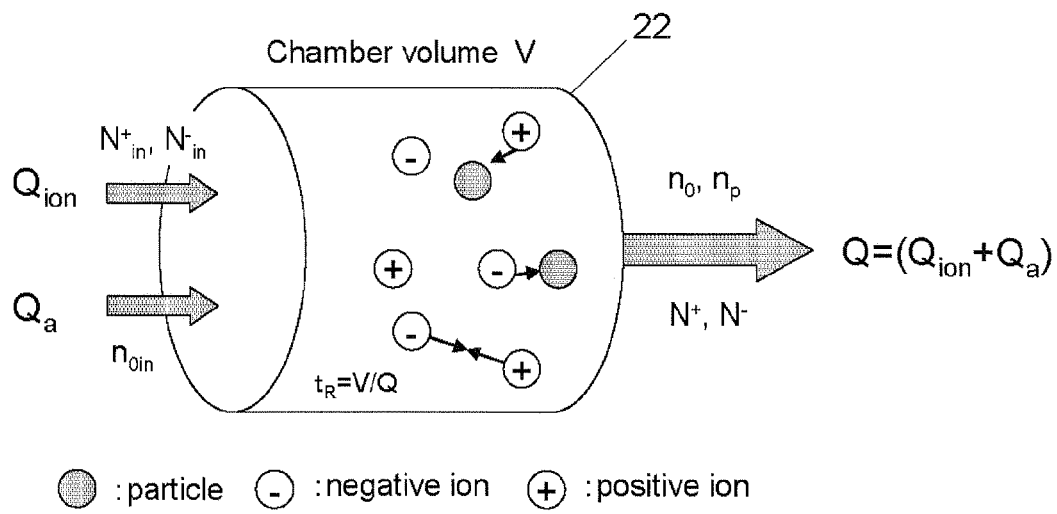
FIG. 3 is a schematic view that shows a charging model in a charging space.

FIG. 3 shows a charging model in a charging space. Here, presume that a completely mixed state (a well-mixed state inside the container, with no concentration difference in ions and particles being caused at any portion inside the container) is formed inside the charging space 22.

α: re-coupling constant of bipolar ions, that is, $1.6 \times 10^{-12}$ [m³/s]

η: coupling coefficient between ions and particles $t_R$[S]: residence time inside the charging space 22, that is, $t_R = V/Q$ V[m³]: capacity of charging space 22

Q[m³/s]: gas flow rate of charging space 22 (ion gas flow rate+charge object gas flow rate)

Under the above-mentioned conditions, changes with time of the cation concentration, anion concentration, non-charged particle concentration and p-valent charged particle concentration were calculated in the following manner. Here, symbol "+" represents a cation, and symbol "−" represents an anion.

(Changes with Time of Cation Concentration)

The change with time ($dN^+/dt$) of cation concentration ($N^+$) is indicated by the following expression:

$$\frac{dN^+}{dt} = -\alpha N^+ N^- - \sum_{p=-\infty}^{\infty} \eta_p^+ n_p N^+ + \frac{(N_{in}^+ - N^+)}{t_R} \quad (1)$$

Left side: Change with time of cation concentration
Right side:
First term: Clear term due to re-coupling of cations and anions
Second term: Clear term due to coupling of cations and particles
Third term: Flow-in/Flow-out term of cations (Changes with Time of Anion Concentration)

The change with time ($dN^-/dt$) of anion concentration ($N^-$) is indicated by the following expression:

$$\frac{dN^-}{dt} = -\alpha N^+ N^- - \sum_{p=-\infty}^{\infty} \eta_p^- n_p N^- + \frac{(N_{in}^- - N^-)}{t_R} \quad (2)$$

Left side: Change with time of anion concentration
Right side:
First term: Clear term due to re-coupling of cations and anions
Second term: Clear term due to coupling of anions and particles
Third term: Flow-in/Flow-out term of anions (Changes with Time of Non-Charged Particle Concentration)

The change with time ($dn_0/dt$) of non-charged particle concentration ($n_0$) is indicated by the following expression:

$$\frac{dn_0}{dt} = \eta_{+1}^- n_{+1} N^- - \eta_0^- n_0 N^- + \eta_{-1}^+ n_{-1} N^+ - \eta_0^+ n_0 N^+ + \frac{(n_{0in} - n_0)}{t_R} \quad (3)$$

Left side: Change with time of non-charged particles
Right side:
First term: Generation term due to re-coupling of anions and +1-valent charged particles
Second term: Clear term due to coupling of anions and non-charged particles
Third term: Generation term due to re-coupling of cations and −1-valent charged particles
Fourth term: Clear term due to coupling of cations and non-charged particles
Fifth term: Flow-in/Flow-out term of non-charged particles (Changes with Time of P-Valent Charged Particle Concentration)

The change with time ($dn_p/dt$) of p-valent non-charged particle concentration ($n_p$) is indicated by the following expression:

$$\frac{dn_p}{dt} = \eta_{p+1}^- n_{p+1} N^- - \eta_p^- n_p N^- + \eta_{p-1}^+ n_{p-1} N^+ - \eta_p^+ n_p N^+ + \frac{(n_{pin} - n_p)}{t_R} \quad (4)$$

Left side: Change with time of p-valent charged particles

Right side:

First term: Generation term due to re-coupling of anions and p+1-valent charged particles Second term: Clear term due to coupling of anions and p-valent charged particles Third term: Generation term due to re-coupling of cations and p−1-valent charged particles Fourth term: Clear term due to coupling of cations and p-valent charged particles Fifth term: Flow-in/Flow-out term of p-valent charged particles Here, η represents a coupling coefficient between ions and particles, and is calculated by the following expression described in Non-Patent Document 1:

$$\eta_p^s = \frac{\pi C_{ion}^s \xi \delta^2 \exp\{-\phi(\delta)/kT\}}{1 + \exp\{-\phi(\delta)/kT\} \frac{C_{ion}^s \xi \delta^2}{4 D_{ion}^s a} \int_0^{a/b} \exp\{\phi(a/x)/kT\} dx}$$

Here, symbol "s" represents "+" or "−".

The means of the respective symbols are explained as follows:

Cion represents thermal motion velocity of an ion, and is indicated by the following expression:

$$C_{ion}^s = \sqrt{8kT/\pi(M_{ion}^s/N_a)}$$

Here, k represents Boltzmann's constant, T represents the absolute temperature, and Mion represents the molecular weight of an ion, and M$^+$ion=0.109 (kg/mol) and M$^-$ion=0.050 (kg/mol) were used. Na represents Avogadro's number. C$^+$ion=2.38×10$^2$ (m/s) and C$^-$ion=3.52×10$^2$ (m/s) were used as numeric values of Cion.

Here, ξ represents the rate of the number of ions that have reached a particle relative to the number of outgoing ions from a limiting sphere.

Here, δ represents the radius of the limiting sphere, and is indicated by the following expression:

$$\delta^s = \frac{a^3}{\lambda_{ion}^{s2}} \left\{ \frac{1}{5}\left(1 + \frac{\lambda_{ion}^s}{a}\right)^5 - \frac{1}{3}\left(1 + \frac{\lambda_{ion}^{s2}}{a^2}\right)\left(1 + \frac{\lambda_{ion}^s}{a}\right)^3 + \frac{2}{15}\left(1 + \frac{\lambda_{ion}^{s2}}{a^2}\right)^{5/2} \right\}$$

Here, λion represents the average free process of an ion when the ion collides with a gas molecule, and is indicated by the following expression:

$$\lambda_{ion}^s = 1.329 \frac{Z_{ion}^2}{e} \sqrt{\frac{kTM_{ion}^s M_{air}}{(M_{ion}^s + M_{air})N_a}}$$

Here, Zion represents the electric mobility of an ion, and Z$^+$ion=1.4×10$^{-4}$(m$^2$V/s) and Z$^-$ion=1.9×10$^{-4}$(m$^2$V/s) were used as numeric values of Zion. Mair represents the molecular weight of air. Here, λ$^+$ion=1.44×10$^{-8}$(m) and λ$^-$ion=1.79×10$^{-8}$(m) were used as numeric values of λion. Moreover, "a" represents the radius of a particle.

Here, φ represents electrostatic potential, and is indicated as follows:

$$\phi(r) = \int_r^\infty F(r) dr = \frac{pe^2}{4\pi\varepsilon_0 r} - \frac{\varepsilon_1 - 1}{\varepsilon_1 + 1} \frac{e^2}{8\pi\varepsilon_0} \frac{a^3}{r^2(r^2 - a^2)}$$

Here, ε$_0$ represents permittivity, that is, 8.855×10$^{-12}$ F/m, ε$_1$ represents relative permittivity, and "r" represents a distance between the center of a particle and the center of an ion.

Dion is a diffusion coefficient of ions, and represented as follows:

$$D_{ion}^s = kTZ_{ion}^s/e$$

D$^+$ion=3.35×10$^{-6}$(m$^2$/s) and D$^-$ion=4.90×10$^{-6}$(m$^2$/s) were used as numeric values of Dion.

Here, x=a/r, and represents a non-dimensional distance between the center of a particle and the center of an ion.

Moreover, "b" represents a distance from the center of a particle to a tangential line drawn on the orbit of an ion, corresponding to an intersection point between the limiting sphere and the orbit of the ion.

Figure 4:
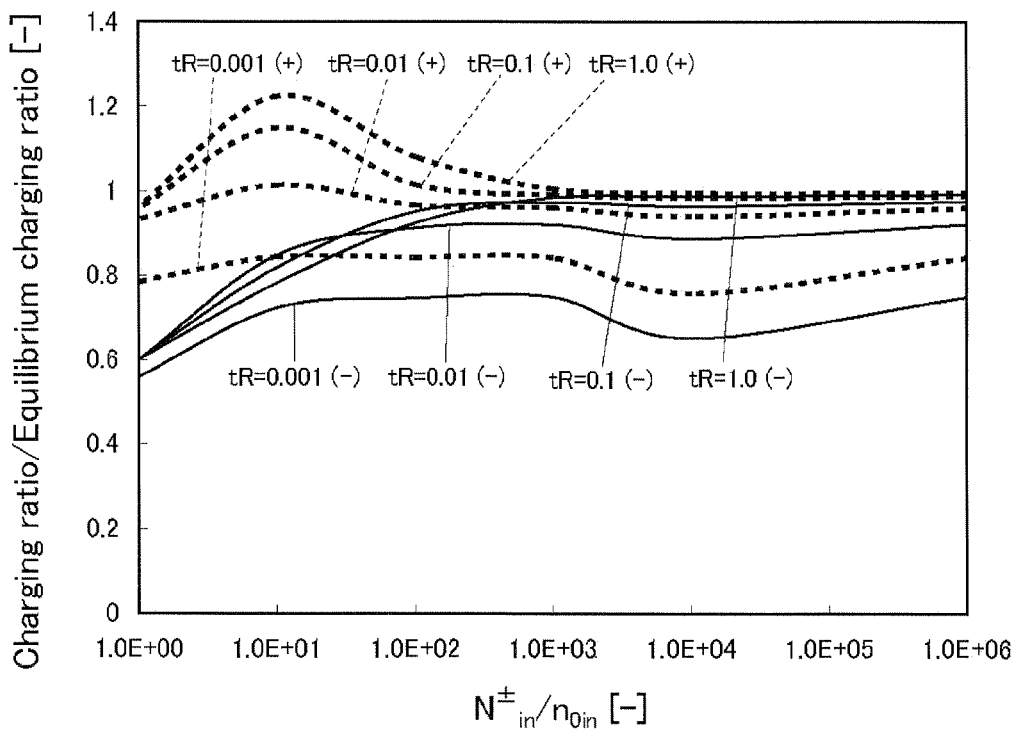
FIG. 4 is a graph that shows the results of charging rate simulations in the charging space relative to various residence times.

Based upon these expressions, N$^\pm_{in}$/n$_{0in}$ (the ratio of positive or negative initial ion concentration N$^\pm_{in}$ relative to charge object concentration n$_{0in}$) was plotted on the axis of abscissas, while the charging ratio/Equilibrium was plotted on the axis of ordinates, for every charging period of time t$_R$, so that the results shown in FIG. 4 were obtained.

A specific method of how to find the results shown in FIG. 4 is explained below: For example, in the case of calculations between N$^\pm_{in}$/n$_{0in}$=1.0×10$^3$ and tR=0.1, upon calculating the positive charge, calculation conditions, such as N$^+_{in}$=1.0×10$^9$ and n$_{0in}$=1.0×10$^6$, are inputted, with the residence time tR of an ionization device to be calculated being determined as 0.1. Moreover, upon calculating the negative charge, calculation conditions, such as N$^-_{in}$=1.0×10$^9$ and n$_{0in}$=1.0×10$^6$, are inputted. These input conditions are successively inputted in accordance with target conditions, and the change in ion concentration and the charging ratio in response to the elapsed time since particles have started entering the ionization device are calculated. Since the calculations have started under the condition that no particles exist in the ionization device although ions exist therein, values at the time when the particle concentration has reached a target particle concentration to attain a stable charged state are taken out and plotted. The results of calculations are set on the assumption that maximum 10 ions (10-valent) can be coupled to a single particle. Therefore, the plotting processes are carried out by using the sum of charging ratios up to the 10-valent for each of the polarities.

Here, the equilibrium charging ratio is calculated based upon a theoretical expression (when sufficiently more ions than particles exist with a sufficient residence period of time) on page 112 of Non-Patent Document 1, and in this expression also, by using the sum of charging ratios up to the 10-valent, the ratio relative to the charging ratio of each of the aforementioned calculation expressions (1) to (4) of the ionization device is adopted.

This graph indicates a ratio of a charging ratio (positive or negative) in the ionization device in accordance with one embodiment of the present invention in the case of a certain particle size (100 nm in this case) relative to a charging ratio (positive or negative) in the case of the same particle size obtained by the existing bipolar equilibrium charging expression shown in Non-Patent Document 1. In the case where the value of a positively-charged particle in the present invention is indicated, it is compared with the value of the positively-charged particle in the expression of Non-Patent Document 1, and in the case where the value of a negatively-charged particle is indicated, the ratio relative to the negatively-charged particle therein is used.

It is indicated that when the charging ratio/equilibrium charging ratio becomes 1, a stable charging operation is achieved. The results shown in FIG. 4 indicate that when the residence time $t_R$ is 0.1 or more, it becomes possible to achieve a stable charging operation under a condition that $N^{\pm}_{in}/n_{0in}$ is $1 \times 10^2$ or more.

What is claimed is:

1. An ionization device comprising:
   an ionization chamber provided with a discharge electrode and an opposing electrode installed inside a case having an ionization gas introducing inlet, with an orifice, which communicates with the outside of the ionization chamber, being formed through the opposing electrode at a position opposing a tip end of the discharge electrode; and
   a charging chamber, disposed adjacent to the ionization chamber on the orifice side thereof, having a charge object introduction portion, in which the charge object is charged by ions discharged from the orifice to be formed into ions,
   wherein an introducing inlet of the charge object introduction portion is disposed near the outlet of the orifice, and
   wherein a size of the orifice and a pressure between the ionization chamber and the charging chamber are so set that the charge object is sucked into the charging chamber by negative pressure generated by a gas, which contains ions, sprayed from the outlet of the orifice into the charging chamber with the pressure of the ionization chamber higher than that of the charging chamber.

2. The ionization device according to claim 1, wherein the charge object introduction portion is arranged so as to introduce the charge object in a direction orthogonal to the spraying direction of ions by the orifice.

3. The ionization device according to claim 1, wherein the ionization chamber is pressurized so that the ionization chamber has a higher pressure than the charging chamber.

4. The ionization device according to claim 3, wherein the charging chamber is provided with a suction pump on the downstream side thereof so that the ionization chamber has a higher pressure than the charging chamber.

5. The ionization device according to claim 1, wherein the charging chamber is provided with a suction pump on the downstream side thereof so that the ionization chamber has a higher pressure than the charging chamber.

* * * * *